United States Patent

Amano et al.

[11] 4,189,607
[45] Feb. 19, 1980

[54] ANILIONOTROPONE DERIVATIVES

[75] Inventors: Takehiro Amano, Urawa; Kensei Yoshikawa, Kitamoto; Jiro Sawada, Kodaira; Michitada Sasajima, Higashimurayama, all of Japan

[73] Assignee: Taisho Pharmaceutical Co., Ltd., Tokyo, Japan

[21] Appl. No.: 24,110

[22] Filed: Mar. 26, 1979

[51] Int. Cl.² .................... C07C 101/453; A01N 9/20
[52] U.S. Cl. ........................... 562/457; 424/319
[58] Field of Search ............ 562/457; 560/48; 424/309, 319

[56] References Cited

U.S. PATENT DOCUMENTS

| | | | |
|---|---|---|---|
| 3,894,080 | 7/1975 | Diamond | 562/457 |
| 3,957,850 | 5/1976 | Bouchara | 562/457 |
| 4,125,625 | 11/1978 | Bagli et al. | 562/457 |

Primary Examiner—Joseph E. Evans
Assistant Examiner—James H. Reamer
Attorney, Agent, or Firm—Kenway & Jenney

[57] ABSTRACT

Anilinotropone derivatives represented by the following formula:

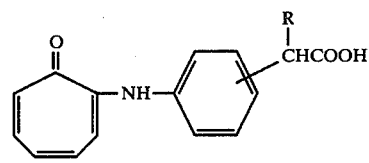

wherein R is hydrogen or methyl and pharmaceutically acceptable salts thereof are disclosed. They exhibit anti-inflammatory and analgesic activity with low gastrointestinal action.

7 Claims, No Drawings

ANILIONOTROPONE DERIVATIVES

BACKGROUND OF THE INVENTION

Among the known anilinotropone derivatives, only 2-(p-aminoalkoxy)anilinotropones are known to have coronary vasodilating and anti-hypertensive activity as described in *Chem. Pharm. Bull.* 22, 514 (1974).

SUMMARY OF THE INVENTION

The present invention relates to anilinotropone derivates represented by the following general formula:

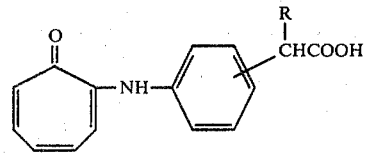

wherein R is hydrogen or methyl and the pharmaceutically acceptable salts thereof.

It has been discovered that the novel compounds of the present invention have excellent anti-inflammatory and analgesic activity and low gastrointestinal action which known anti-inflammatory agents have in proportion to their anti-inflammatory activity.

Accordingly, it is an object of the present invention to provide these novel compounds valuable as medicines possessing excellent anti-inflammatory and analgesic activity and reduced gastrointestinal action.

DESCRIPTION OF THE PREFERRED EMBODIMENT

The anilinotropone derivatives the present invention represented by the general formula (I) may be prepared by reacting a tropone derivative represented by the following general formula:

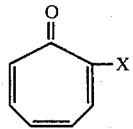

wherein X is a halogen atom such as fluorine, chlorine or bromine, a sulfonyloxy group such as a tosyloxy group, or an alkoxy group such as methoxy with an aniline derivative represented by the following general formula:

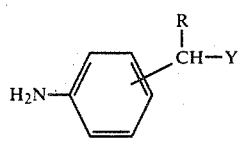

wherein R is hydrogen or methyl and Y is a carboxyl-group or a group that can be converted to carboxyl group, such as an ester or nitrile group and subjecting the reaction product to hydrolysis or the like when Y is not a carboxyl group.

In practicing the above reaction, a basic condensing agent such as potassium carbonate, sodium acetate or triethylamine may be used and, in order that the reaction proceed easily, an iodide such as sodium iodide or potassium iodide Ullmann catalyst such as activated copper or copper sulfate may also be used. As the reaction solvent, there may be used an organic solvent such as benzene, ethanol, tert-butyl alcohol, tetrahydrofuran, acetone, dimethylsulfoxide or N,N-dimethylformamide. It is preferred that the reaction be carried out at room temperature or at a refluxing temperature.

The pharmaceutically acceptable salts of the compounds of the formula (I) include, but are not limited to, the corresponding alkali metal salts such as sodium and potassium salts, alkaline earth metal salts, such as barium and calcium salts, and unsubstituted and substituted ammonium salts. A compound of the formula (I) may be converted into a desired salt by treating with alkali metal base, alkaline earth metal base, or unsubstituted or substituted ammonium base in a known manner.

The compounds of the present invention may be used as anti-inflammatory, analgesic and anti-pyretic agents in mammals. For these purposes, a compound of the present invention may be administered orally in a conventional dosage form such as tablet, capsule or powder prepared according to conventional pharmaceutical practice. A single dose, or preferably 2 to 4 divided daily doses, provided on a basis of about 2 to 40 mg/kg/day, is appropriate.

The compounds of the present invention have extremely low toxicity. The minimum lethal dose of mice or rats is in excess of 1000 mg/kg of the body weight.

Experiments made on pharmaceutical properties of the compounds of the present invention and on a prior art compound (phenylbutazone) are summarized below. In these experiments, "Cpd. 1", "Cpd. 2" and "Cpd. 3" refer to 2-[p-(2-troponylamino)phenyl]propionic acid, 2-[m-(2-troponylamino)phenyl]propionic acid and phenylbutazone, respectively.

Experiment 1: Anti-inflammatory activity

Anti-inflammatory activity was evaluated by the method of rat paw edema (Winter et al, *J. Pharmacol. Exp. Ther.*, 141, 369 (1963)). Six male Wistar strain rats were used in each group and the volume of each paw was measured four hours after injection of carrageenin. The results are shown in Tables 1 and 2.

Table 1

|         | Dose (mg/kg, p.o.) | Inhibition (%) |
|---------|---------------------|----------------|
| Cpd. 1  | 25                  | 56.8           |
| Cpd. 1  | 50                  | 50.9           |
| Cpd. 1  | 100                 | 61.0           |
| Cpd. 3  | 25                  | 22.4           |
| Cpd. 3  | 50                  | 34.7           |
| Cpd. 3  | 100                 | 54.5           |

Table 2

|               | Dose (mg/kg, p.o.) | Inhibition (%) |
|---------------|---------------------|----------------|
| Cpd. 2        | 100                 | 43.0           |
| Cpd. 2-Ca salt| 100                 | 43.2           |
| Cpd. 3        | 100                 | 32.5           |

Experiment 2: Analgesic activity

Male Wistar strain rats in groups of six each were used for the evaluation of analgesic activity by the method of Randall-Selitto (*Arch. Intern. Pharmacodyn.*, 111, 409 (1957)) with slight modification. In a graph where the load was plotted on the ordinate and the time was plotted on the abscissa, the curve obtained when Cpd. 1 was orally administered in a dose of 25 mg/kg was substantially in agreement with the curve obtained when Cpd. 3 was orally administered in a dose of 100 mg/kg. Similar results were obtained when Cpd. 1 was administered in a dose of 50 mg/kg and the Cpd 3 was administered in a dose of 200 mg/kg.

Experiment 3: Analgesic activity

Male ddY strain mice in groups of ten each were used for evaluation of analgesic activity by the acetic acid writhing test (Koster et al, Federation Proc., 18, 412 (1959). The results are shown in Tables 3 and 4.

Table 3

|  | Dose (mg/kg. p.o.) | Inhibition (%) |
|---|---|---|
| Cpd. 1 | 100 | 54.8 |
| Cpd. 3 | 200 | 18.5 |

Table 4

|  | Dose (mg/kg, p.o.) | Inhibition (%) |
|---|---|---|
| Cpd. 2 | 100 | 31.2 |
| Cpd. 2-Ca salt | 100 | 31.2 |
| Cpd. 3 | 100 | 10.7 |

Experiment 4: Gastric ulcerogenicity

Immediately after the completion of the test described in Experiment 1, the test compound was orally administered to the test rats in a dose administered in Experiment 1, and fasting was continued for 18 hours prior to autopsy and evaluation of gastric lesions. The gastric lesions induced was expressed as incidence (number of rats with gastric lesions/number of the test rats) and lesion index (sum of areas damaged). The results are shown in Tables 5 and 6.

Table 5

|  | Dose (mg/kg, p.o.) | Incidence | Lesion index (mm$^2$) |
|---|---|---|---|
| Cpd. 1 | 25 + 50 | 0/6 | 0 |
| Cpd. 1 | 50 + 100 | 1/6 | 0.02 ± 0.017 |
| Cpd. 1 | 100 + 200 | 4/6 | 0.52 ± 0.17 |
| Cpd. 3 | 25 + 50 | 3/6 | 0.02 ± 0.014 |
| Cpd. 3 | 50 + 100 | 6/6 | 1.43 ± 0.43 |
| Cpd. 3 | 100 + 200 | 6/6 | 6.82 ± 1.40 |

Table 6

|  | Dose (mg/kg, p.o.) | Incidence | Lesion index (mm$^2$) |
|---|---|---|---|
| Cpd. 2 | 100 + 200 | 0/6 | 0 |
| Cpd. 2-Ca salt | 100 + 200 | 2/6 | 0.12 ± 0.10 |
| Cpd. 3 | 100 + 200 | 6/6 | 7.70 ± 3.23 |

The following examples are illustrative of the present invention and are not intended in any way to limit the invention, the scope of which is defined by the appended claims.

EXAMPLE 1

A mixture of 8.3 g of 2-tosyltropone, 4.5 g of p-aminophenylacetic acid and 9 ml of triethylamine in 200 ml of tert-butylalcohol was refluxed for 24 hours. The mixture was concentrated and acidified with 2 N hydrochloric acid, followed by extraction with dichloromethane. The dichloromethane solution was extracted with a saturated sodium bicarbonate aqueous solution. The aqueous layer was acidified and extracted with dichloromethane. The dichloromethane solution was washed with water and dried over anhydrous magnesium sulfate and evaporated to give a yellow crystalline solid, which was recrystallized from ethanol to yield 4.6 g of p-(2-troponylamino) phenylacetic acid; m.p. 175°–176° C.; Analysis—Calculated for $C_{15}H_{13}NO_3$: C 70.58%, H 5.13%, N 5.49%; Found: C70.34%, H 5.30%, N 5.55%.

EXAMPLE 2

A mixture of 2.8 g of 2-chlorotropone, 3.3 g of 2-(p-aminophenyl)propionic acid, 4.9 g of sodium acetate, and 0.20 g of sodium iodide in 100 ml of N,N-dimethylformamide was stirred at 80°–90° C. for 8 hours. The mixture was cooled and acidified with 2 N hydrochloric acid, followed by extraction with dichloromethane. The dichloromethane solution was extracted with a saturated aqueous sodium bicarbonate solution. The aqueous layer was acidified and extracted with dichloromethane. The dichloromethane solution was washed with water, dried over anhydrous magnesium sulfate and evaporated to give a yellow crystalline solid, which was recrystallized from ethanol to yield 3.8 g of 2-(p-troponylaminophenyl)propionic acid; m.p. 185°–186° C., Analysis—Calculated for $C_{16}H_{15}NO_3$: C 71,36%, H 5.61%, N 5.20%, Found: C 71.20%, H5.60%, N 5.27%.

EXAMPLE 3

A mixture of 2.8 g of 2-chlorotropone, 3.3 g of 2-(m-aminophenyl)propionic acid, 4.9 g of sodium acetate and 0.20 g of potassium iodide in 50 ml of N,N-dimethylformamide was stirred at 80°–90° C. for 8 hours. The mixture was concentrated and acidified with 6 N hydrochloric acid, followed by extraction with dichloromethane. The dichloromethane solution was extracted with a saturated aqueous sodium bicarbonate solution. The aqueous layer was adjusted to pH 4–5 with 6 N hydrochloric acid and extracted with dichloromethane. The extract was washed with water, dried over anhydrous magnesium sulfate and evaporated to give a yellow oil, which was chromatographed on silica gel with chloroform and crystallize from benzene to give 3.0 g of m-(2-troponylamino)phenylacetic acid; m.p. 97°–98° C.; Analysis13 Calculated for $C_{15}H_{13}NO_3$: C 70.58%, H 5.13%, N 5.49%, Found: C 70.36%, H 5.20%, N 5.54%.

EXAMPLE 4

To a mixture of 4.6 g of 2-(4-chloro-3-nitrophenyl) propionic acid and 250 mg of 10% palladium-on-charcoal in 50 ml of ethanol, was added dropwise 2.5 g of hydrazine hydrate under a stream of nitrogen. After the completion of the addition, the mixture was stirred at room temperature for one hour and then refluxed for 6 hours. The resulting mixture was cooled to room temperature, mixed with 250 mg of 10% palladium-on-charcoal and 2.5 g of hydrazine hydrate, and refluxed for 6 hours. After filtration, the filtrate was evaporated and dissolved in 20 ml of water. The aqueous solution was adjusted to pH 5–6 with 6 N hydrochloric acid and then concentrated to a volume of 20 ml. On standing overnight at room temperature, 3.0 g of 2-(m-aminophenyl)propionic acid was obtained; m.p. 98°–100° C.; Analysis—Calculated for $C_9H_{11}NO_2$: C 65.43%, H 6.71%, N 8.48%, Found C 65.41%, H 6.72%, N 8.48%.

A mixture of 7.03 g of 2-chlorotropone, 8.3 g of 2-(m-aminophenyl)propionic acid, 12.3 g of sodium acetate and 0.83 g of sodium iodide in 150 ml of N,N-dimethylformamide was stirred at 90°–100° C. for 6 hours, followed by the procedure exemplified in Example 3 to give 8.7 g of 2-]m-(2-troponylamino)phenyl]propionic acid as a yellow oil; Analysis—Calculated for $C_{16}H_{15}NO_3$: C 71.36%, H 5.61%, N 5.20%; Found: C 71.27%, H 5.60%, N 5.26%.

To a solution of 10.0 g of 2-[m-(2-troponylamino)-phenyl]propionic acid in 30 ml of dichloromethane, was added 30 ml of water. The mixture was adjusted to pH 7.0 with 0.01 N sodium hydroxide solution. The aqueous layer which separated was collected, and 2.22 g of calcium chloride in 10 ml of water was added dropwise with stirring to form a yellow precipitate. The precipitate was collected on a filter, washed with cold water and dried to give 10.2 g of calcium 2-[m-(2-troponylamino)phenyl]propionate. Recrystallization from aqueous ethanol gave a yellow powder which decomposed at 240°–242° C.

What is claimed is:

1. Anilionotropone derivatives represented by the following formula:

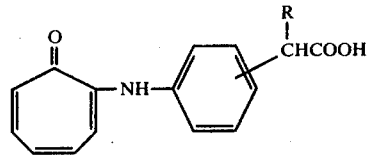

wherein R is hydrogen or methyl, and pharmaceutically acceptable salts thereof.

2. A compound according to claim 1 wherein R is hydrogen.

3. A compound according to claim 1 wherein R is methyl.

4. A compound of claim 2 which is p-(2-troponylamido)phenylacetic acid or a pharmaceutically acceptable salt thereof.

5. A compound according to claim 2 which is m-(2-troponylamino)phenylacetic acid or a pharmaceutically acceptable salt thereof.

6. A compound according to claim 3 which is 2[p-(2-troponylamino)phenyl]propionic acid or a pharmaceutically acceptable salt thereof.

7. A compound according to claim 3 which is 2-[m-(2-troponylamino)phenyl]propionic acid or a pharmaceutically acceptable salt thereof.

* * * * *

UNITED STATES PATENT AND TRADEMARK OFFICE
CERTIFICATE OF CORRECTION

PATENT NO. : 4,189,607

DATED : February 19, 1980

INVENTOR(S) : Amano et al.

It is certified that error appears in the above-identified patent and that said Letters Patent are hereby corrected as shown below:

Column 1, line 59, "carboxyl-" should read --carboxyl--;

Column 4, line 65, "}" should read --[--;

Claim 4, line 2, "troponylamido)phenylacetic" should read --troponylamino)phenylacetic--.

Signed and Sealed this

Sixth Day of May 1980

[SEAL]

Attest:

SIDNEY A. DIAMOND

Attesting Officer

Commissioner of Patents and Trademarks